(12) United States Patent
Rai et al.

(10) Patent No.: US 8,350,006 B2
(45) Date of Patent: Jan. 8, 2013

(54) METHODS FOR DETERMINING THE BIOACTIVITY OF TGF-β IN A COMPOSITION

(75) Inventors: Gyan P. Rai, Newburgh, IN (US); Francisco J. Rosales, Newburgh, IN (US); Zeina E. Jouni, Evansville, IN (US); Rosaline Waworuntu, Evansville, IN (US)

(73) Assignee: Mead Johnson Nutrition Company, Evansville, IN (US)

( * ) Notice: Subject to any disclaimer, the term of this patent is extended or adjusted under 35 U.S.C. 154(b) by 599 days.

(21) Appl. No.: 12/371,045

(22) Filed: Feb. 13, 2009

(65) Prior Publication Data

US 2010/0105080 A1    Apr. 29, 2010

Related U.S. Application Data

(60) Provisional application No. 61/108,309, filed on Oct. 24, 2008.

(51) Int. Cl.
C07K 14/495 (2006.01)
A23J 1/20 (2006.01)
G01N 33/04 (2006.01)
C12N 5/0783 (2010.01)

(52) U.S. Cl. .......... 530/350; 530/412; 436/22; 435/7.24
(58) Field of Classification Search .................. None
See application file for complete search history.

(56) References Cited

U.S. PATENT DOCUMENTS

| | | | |
|---|---|---|---|
| 5,290,571 A | 3/1994 | Bounous et al. |
| 5,451,412 A | 9/1995 | Bounous et al. |
| 5,461,033 A | 10/1995 | Donnet et al. |
| 5,866,418 A | 2/1999 | Ballard et al. |
| 5,952,295 A | 9/1999 | Arnaud-Battandier et al. |
| 6,194,208 B1 | 2/2001 | Belford et al. |
| 6,319,522 B1 | 11/2001 | Ballard et al. |
| 6,395,494 B1 | 5/2002 | Grainger et al. |
| 6,447,808 B2 | 9/2002 | Ballard et al. |
| 6,733,770 B1 | 5/2004 | Garcia-Rodenas et al. |
| 7,094,550 B2 | 8/2006 | Grainger et al. |
| 7,141,262 B2 | 11/2006 | Maubois et al. |
| 2003/0232057 A1 | 12/2003 | Turini et al. |
| 2004/0102377 A1 | 5/2004 | Perrin et al. |
| 2005/0250697 A1 | 11/2005 | Maubois et al. |
| 2006/0293228 A1 | 12/2006 | Bhatnagar |

FOREIGN PATENT DOCUMENTS

| | | |
|---|---|---|
| EP | 0313515 | 3/1992 |
| EP | 0339656 | 11/1994 |
| EP | 0374390 | 6/1995 |
| EP | 0527283 | 11/1997 |
| EP | 0852913 | 7/1998 |
| EP | 0759029 | 7/1999 |
| EP | 1034704 | 9/2000 |
| EP | 1161152 | 10/2004 |
| EP | 0545946 | 1/2005 |
| EP | 1218410 | 6/2005 |
| EP | 1345624 | 6/2006 |
| EP | 1779863 | 5/2007 |
| WO | 9200994 | 1/1992 |
| WO | 9818816 | 5/1998 |
| WO | 0054603 | 9/2000 |
| WO | 0125276 | 4/2001 |
| WO | 02051437 | 7/2002 |
| WO | 02083164 | 10/2002 |
| WO | 2005039318 | 5/2005 |

OTHER PUBLICATIONS

Harris et al. "Centrifugation" Section 2.1, In, Protein Purification Methods: A Practical Approach, Harris et al. (Eds.), Sep. 1989, IRL Press, Oxford, UK, pp. 71-72.*
Rogers et al. Transforming growth factor beta in bovine milk: concentration, stability and molecular mass forms. J Endocrinol. Oct. 1996;151(1):77-86.*
Hawkes, et al., Transforming Growth Factor Beta in Human Milk Does Not Change in Response to Modest Intakes of Docosahexaenoic Acid, Lipids, vol. 36, No. 10 (2001) pp. 1179-1182. abstract, subjects and methods.
Zugmaier, et al., Transforming growth factors type beta 1 and beta 2 are equipotent growth inhibitors of human breast cancer cell lines, J. Cell. Physiol., Nov. 1989; 141(2); 353-61, abstract.

* cited by examiner

*Primary Examiner* — David Romeo
(74) *Attorney, Agent, or Firm* — Waddey & Patterson, P.C.; James R. Cartiglia; Rebecca M. Barnett

(57) ABSTRACT

A novel method for determining the bioactivity of TGF-β in a sample of milk, raw protein source, or nutritional composition is provided. The method includes particular reconstitution steps, centrifugation steps, incubation steps, and activation steps. The bioactivity of the TGF-β in the sample may be measured in a HT-2 cell bioassay or a cellomics bioassay.

8 Claims, 5 Drawing Sheets

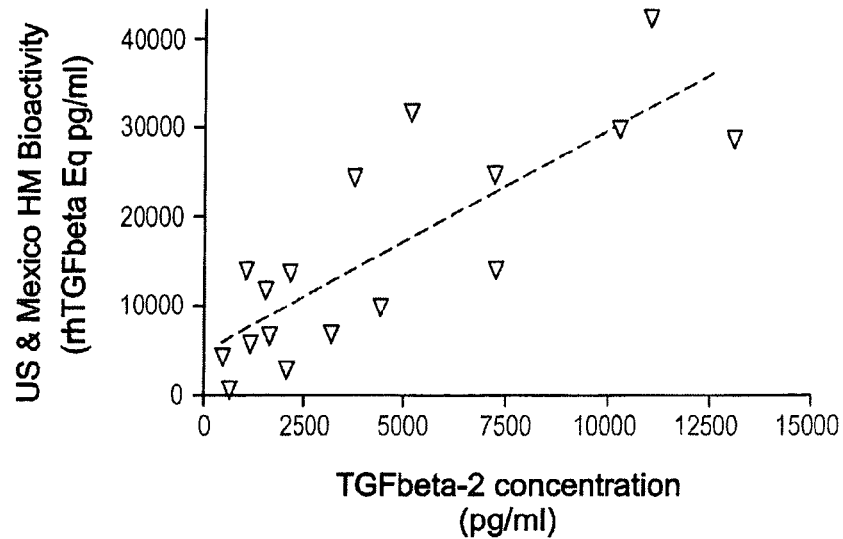

FIG. 2C

| Linear Regression | Mexico HM rhTGFbeta2 Equivalency (pg/ml) | US HM rhTGFbeta2 Equivalency (pg/ml) | US & Mexico HM rhTGFbeta2 Equivalency (pg/ml) |
|---|---|---|---|
| Best-fit values | | | |
| Slope | 2.792 ± 0.8179 | 2.502 ± 0.2948 | 2.491 ± 0.4589 |
| Y-intercept | 8266 ± 4297 | 775.0 ± 1874 | 4897 ± 2691 |
| X-intercept | -2961 | -309.8 | -1966 |
| 1/slope | 0.3582 | 0.3997 | 0.4014 |
| 95% Confidence Intervals | | | |
| Slope | 0.7905 to 4.793 | 1.805 to 3.199 | 1.513 to 3.469 |
| Y-intercept when X=0.0 | -2248 to 18780 | -3657 to 5207 | -836.9 to 10630 |
| X-intercept when Y=0.0 | -21220 to 525.3 | -2703 to 1220 | -6528 to 259.7 |
| Goodness of Fit | | | |
| $r^2$ | 0.6601 | 0.9114 | 0.6627 |
| Sy.x | 7813 | 3667 | 7237 |
| Is slope significantly non-zero? | | | |
| F | 11.65 | 72.03 | 29.47 |
| DFn, DFd | 1.000, 6.000 | 1.000, 7.000 | 1.000, 15.00 |
| P value | 0.0143 | < 0.0001 | < 0.0001 |
| Deviation from zero? | Significant | Significant | Significant |
| Data | | | |
| Number of X values | 8 | 9 | 17 |
| Maximum number of Y replicates | 1 | 1 | 1 |
| Total number of values | 8 | 9 | 17 |
| Number of missing values | 0 | 0 | 0 |

FIG. 2D

METHODS FOR DETERMINING THE BIOACTIVITY OF TGF-β IN A COMPOSITION

CROSS-REFERENCE TO RELATED APPLICATION

This application claims benefit of the following patent application(s) which is/are hereby incorporated by reference: U.S. Provisional Application Ser. No. 61/108,309 filed Oct. 24, 2008.

BACKGROUND OF THE INVENTION (1) Field of the Invention

The present invention relates generally to methods of determining the bioactivity of transforming growth factor-β (TGF-β) in a composition.

SUMMARY OF THE INVENTION

Briefly, the present invention is directed to a method for determining the bioactivity of TGF-β in a sample of powdered nutritional composition or powdered raw protein source, the method comprising:
a. reconstituting the sample to a concentration of about 140 mg/mL to about 150 mg/mL;
b. centrifuging the reconstituted sample at about 10,000 rpm for about 10 minutes and retaining the supernatant layer;
c. acidifying the supernatant layer to a pH of about 2 to about 3;
d. incubating the supernatant layer for about 15 minutes at room temperature;
e. centrifuging the supernatant layer at about 10,000 rpm for about 10 minutes and retaining the supernatant layer;
f. neutralizing the supernatant layer from step (e) to a pH of about 7 to about 7.5;
g. centrifuging the supernatant layer from step (f) at about 10,000 rpm for about 10 minutes and retaining the supernatant layer;
h. contacting the supernatant layer with HT-2 cells; and
i. determining the concentration at which inhibition of the bioactivity in the HT-2 cells is 50%.

The present invention is also directed, in an embodiment, to a method for determining the bioactivity of TGF-β in a sample of liquid milk, the method comprising:
a. centrifuging the sample at about 13,000 rpm for about 15 minutes;
b. collecting the supernatant layer of the sample and repeating step (a) using the supernatant;
c. collecting the supernatant layer of the sample from step (b) and repeating step (a) using the supernatant of step (b);
d. acidifying the supernatant layer to a pH of about 2 to about 3;
e. incubating the supernatant layer for about 3 hours at room temperature;
f. neutralizing the supernatant layer to a pH of about 7 to about 7.5;
g. centrifuging the supernatant layer from step (f) at about 10,000 rpm for about 10 minutes and retaining the supernatant layer;
h. contacting the supernatant layer with HT-2 cells; and
i. determining the concentration at which inhibition of the bioactivity in the HT-2 cells is 50%.

In another embodiment, the invention is directed to a method for determining the bioactivity of TGF-β in a sample of liquid milk, the method comprising:
a. acidifying the sample to a pH of about 2 to about 3;
b. incubating the sample for about 3 hours at room temperature;
c. neutralizing the sample to a pH of about 7 to about 7.5;
d. centrifuging the sample at about 10,000 rpm for about 5 minutes and retaining the supernatant layer;
e. centrifuging the supernatant layer at about 10,000 rpm for about 5 minutes and retaining the supernatant layer;
f. contacting the supernatant layer of step (e) with HT-2 cells; and
g. determining the concentration at which inhibition of the bioactivity in the HT-2 cells is 50%.

In yet another embodiment, the invention is directed to a method for determining the bioactivity of TGF-β in a sample of powdered nutritional composition or powdered raw protein source, the method comprising:
a. reconstituting the sample to a concentration of about 140 mg/mL to about 150 mg/mL;
b. acidifying the reconstituted sample to a pH of about 2 to about 3;
c. incubating the supernatant layer for about 15 minutes at room temperature;
d. centrifuging the supernatant layer at about 10,000 rpm for about 10 minutes and retaining the supernatant layer;
e. neutralizing the supernatant layer from step (d) to a pH of about 7 to about 7.5;
f. exposing sample to MDA-MB-468 cells in the presence of 1% serum; and
g. analyzing the TGF-β response based upon translocation of GFP-tagged Smad2 from the cytoplasm to the nucleus.

In still another embodiment, the invention is directed to a method for determining the bioactivity of TGF-β in a sample of liquid milk, the method comprising:
a. acidifying the sample to a pH of about 2 to about 3;
b. incubating the sample for about 15 minutes at room temperature;
c. centrifuging the sample at about 10,000 rpm for about 10 minutes and retaining the supernatant layer;
d. neutralizing the supernatant layer from step (c) to a pH of about 7 to about 7.5;
e. exposing sample to MDA-MB-468 cells in the presence of 1% serum; and
f. analyzing the TGF-β response based upon translocation of GFP-tagged Smad2 from the cytoplasm to the nucleus.

BRIEF DESCRIPTION OF THE DRAWINGS

FIGS. 2A-D are equivalency graphs and data.

DETAILED DESCRIPTION OF THE PREFERRED EMBODIMENTS

Figure 1:
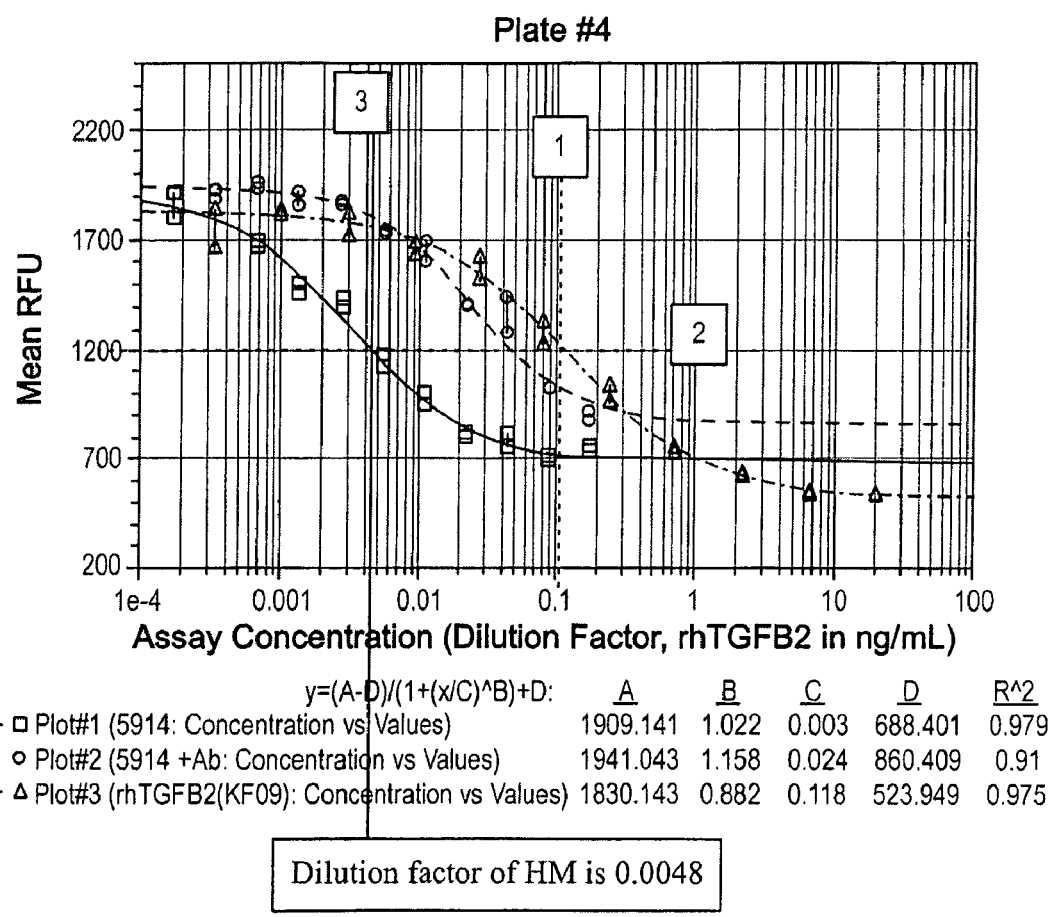
FIG. 1 shows the equivalency of TGF-β bioactivity calculated for a sample having a TGF-β2 activity of 7175.3 pg/mL and $ED_{50}$ of 0.118 ng/mL of rhTGF-β2.
Figure 2A:
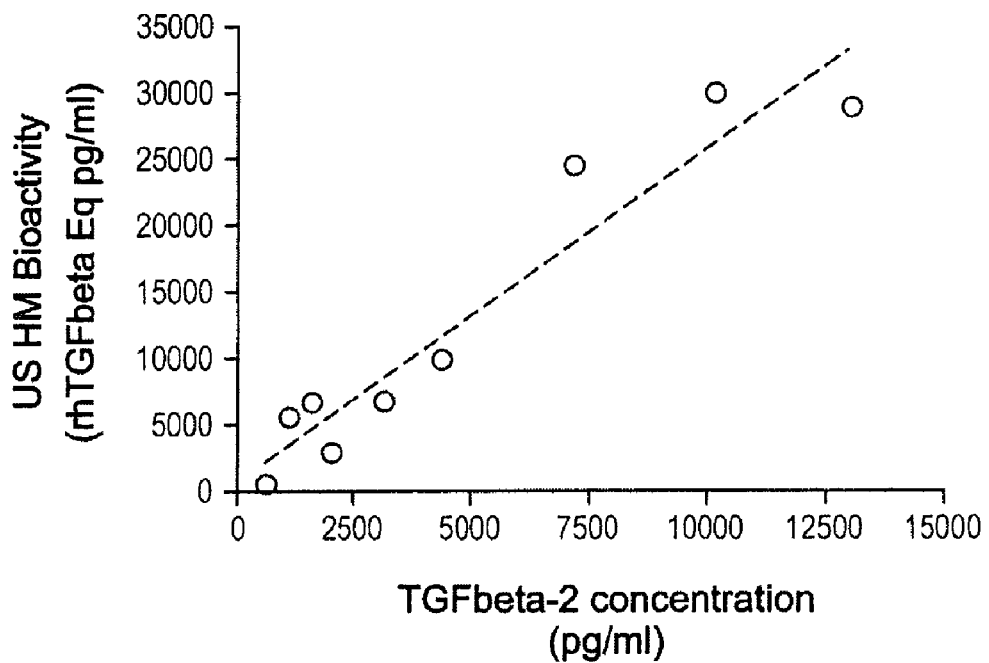
Figure 2B:
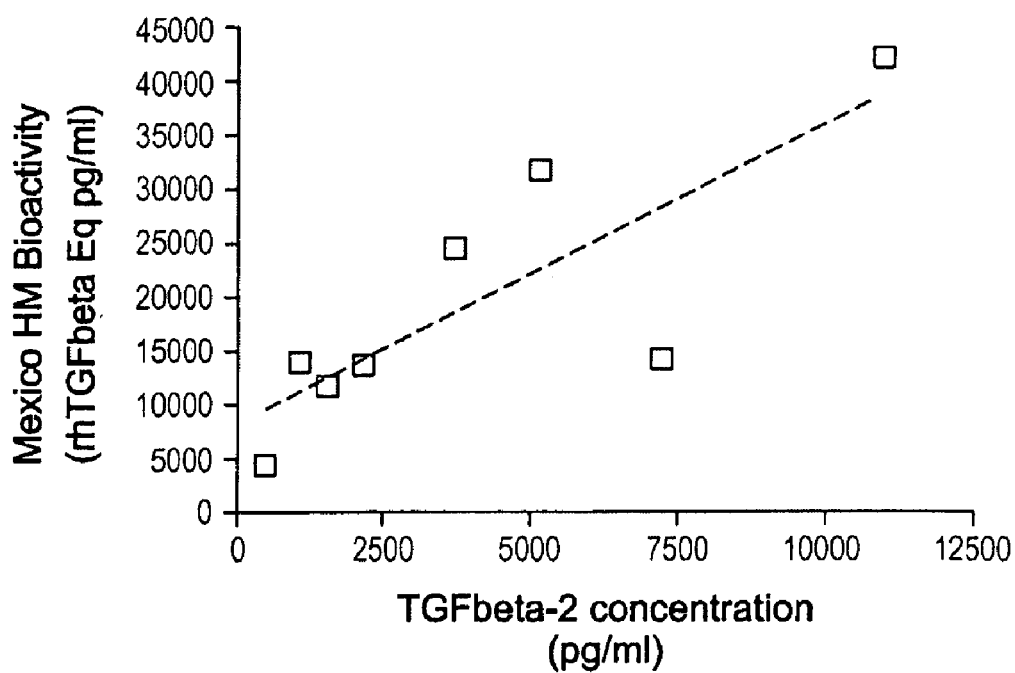

Reference now will be made in detail to the embodiments of the invention, one or more examples of which are set forth below. Each example is provided by way of explanation of the invention, not a limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment.

Thus, it is intended that the present invention covers such modifications and variations as come within the scope of the appended claims and their equivalents. Other objects, features and aspects of the present invention are disclosed in or are obvious from the following detailed description. It is to be understood by one of ordinary skill in the art that the present discussion is a description of exemplary embodiments only, and is not intended as limiting the broader aspects of the present invention.

As set forth above, the present invention relates generally to methods for determining the bioactivity of TGF-β in various samples. References related to such methods may include U.S. Pat. Nos. 6,194,208, 7,094,550 and EP 759,029.

Transforming growth factor-beta (TGF-β) is the general name for a family of polypeptides, the members of which have multifunctional regulatory activities. Three differentially regulated mammalian isoforms (termed TGF-β1, TGF-β2, and TGF-β3) play important roles in a multitude of processes in the developing embryo, infant, child and adult. TGF-β is a 25-kDa homodimeric cytokine known to mediate pleiotropic functions both within the immune system and systemically. TGF-β is expressed in several cell types in the intestinal mucosal including lymphocytes, epithelial cells, macrophages, and stromal cells as well as by T-cells, neutrophils, macrophages, epithelial cells, fibroblasts, platelets, osteoblasts, osteoclasts and others. In addition, TGF-β is present in human breast milk and may influence multiple aspects of infant health and development.

TGF-βs are synthesized as large precursor proteins which consist of an amino-terminal pro-domain, comprising a signal sequence and latency-associated complex, and a mature carboxy-terminal subunit. Biologically active TGF-βs are homodimers which consist of two identical, disulfide-linked mature subunits. Release of the TGF-β homodimer from the latency-associated complex is necessary for TGF-β to exert biological activity on target cells. The nature of the latency-associated complex and the mechanisms responsible for TGF-β release are key to understanding TGF-β biological activity in vivo. In the human gut, this may be accomplished by the action of proteolytic enzymes, pH extremes, heat, calcium, and/or mechanical tearing.

Based on the numerous benefits provided by TGF-β, it is often important that the growth factor is present in, or supplemented into, various nutritional products. For example, certain protein sources in nutritional products may provide a source of TGF-β. Alternatively, if the nutritional product itself does not contain TGF-β, the growth factor may be supplemented into the product. As noted above, however, the release of TGF-β is in its inactive form. The TGF-β present in the protein sources of nutritional products, or added to those nutritional products, is also in its inactive form. It is then activated in the human gut by enzymes, extremes of pH, and/or tearing.

Based on the numerous benefits provided by TGF-β, it is often important that the growth factor is present in, or supplemented into, various liquid nutritional products. Until the present invention, however, there has not been an effective method for determining the bioactivity of TGF-β in a sample of milk, nutritional product, or raw protein source, such as whey protein concentrate. In part, this may be due to high variability within and between studies reporting bioactivity of TGF-β in these compositions. Moreover, there is relatively little knowledge of the factors affecting the reported bioactivity in milk, nutritional products, or raw protein sources.

Thus, the technical problem to be solved by the present invention is to provide an accurate and reproducible method for determining the bioactivity of TGF-β, including both TGF-β1 and TGF-β2, in a composition. In accordance with the present invention, the inventors have discovered a novel method for determining the bioactivity of TGF-β in a sample of milk, nutritional product, or raw protein source.

As set forth above, the method of the invention may be used to determine the bioactivity of TGF-β in milk sources. In this embodiment, the milk may be human milk, bovine milk, goat milk, sheep milk, or any other milk sourced from a mammal.

In another embodiment, the method of the invention may be used to determine the bioactivity of TGF-β in a nutritional product. The nutritional product may be an infant formula. In some embodiments, the nutritional product may be an infant formula. The term "infant formula" applies to a composition in liquid or powdered form intended for use, where necessary, as a substitute for human milk (breast milk substitute) in meeting the normal nutritional requirements of infants. In a separate embodiment, the nutritional product may be a human milk fortifier, meaning it is a composition which is added to human milk in order to enhance the nutritional value of human milk. As a human milk fortifier, the inventive composition may be in powder or liquid form. In another embodiment, the inventive nutritional product may be a follow-up formula. The term "follow-up formula" as used herein refers to foods intended for use as a liquid part of the weaning diet for the infant from the 6$^{th}$ month of life on and for young children. In yet another embodiment, the inventive nutritional product may be a children's nutritional composition. The term "child" or "children" as used herein means persons over the age of 3 years and prior to adolescence. In still another embodiment, the inventive nutritional product may be a growing-up milk. The term "growing-up milk" refers to a broad category of milk-based fortified beverages intended to be used as a part of a diverse diet in order to support the normal growth and development of children from the ages of 1 to 6 years.

In some embodiments, the composition is an acidified product. As used herein, the term "acidified product" refers to a nutritional composition which has a finished equilibrium pH of 4.6 or below and a water activity greater than 0.85. In still another embodiment, the nutritional product may be a medical food. The term "medical food" is defined as a food which is formulated to be consumed or administered enterally under the supervision of a physician and which is intended for the specific dietary management of a disease or condition for which distinctive nutritional requirements, based on recognized scientific principles, are established by medical evaluation. In general, to be considered a medical food, a product must, at a minimum, meet the following criteria: the product must be a food for oral or tube feeding; the product must be labeled for the dietary management of a specific medical disorder, disease or condition for which there are distinctive nutritional requirements; and the product must be intended to be used under medical supervision.

In yet another embodiment, the method of the invention may be used to determine the bioactivity of TGF-β in a raw protein source, such as whey protein concentrate, non-fat dry milk, or casein protein.

The composition of the invention may be provided in any form known in the art, such as a powder, a gel, a suspension, a paste, a solid, a liquid, a liquid concentrate, or a ready-to-use product.

In a method of the invention, the bioactivity of TGF-β1 and TGF-β2 is measured using a HT-2 cell bioassay. Bioactivity is determined as a measure of the IC50 value of the composition tested. The IC50 value is a measure of the effectiveness of a composition in inhibiting biological or biochemical function by half. In this case, the IC50 value is the concentration at which inhibition of the bioactivity in the HT-2 cells is 50%.

The HT-2 cell line is a clone murine T-helper, factor dependent line established by Dr. James Watson (J. Exp. Med. 1979; 150:1510). The bioassay measures the inhibition of cell growth over a dose-response of TGF-β, which is usually a two-fold sequential dilution. The bioassay measures the activity of TGF-β in inhibiting the growth of these cells that have been activated with murine interleukin-4 (mIL-4). This cell bioassay has been shown to be highly reproducible and accurate when compared to the growth inhibition of mink lung epithelial cells (Mv1Lu bioassay). The bioassay is demonstrated as highly sensitive to picomolar concentrations of TGF-β inhibiting the S-phase progression of HT-2 cells stimulated with IL-4.

Prior to the present invention, no process had been yet developed regarding the preparation of samples of nutritional products, raw protein sources, or milk sources for a HT-2 cell bioassay measuring TGF-β bioactivity. The present inventors have developed a novel method of preparing these compositions and measuring TGF-β1 and TGF-β2 bioactivity therein.

In some embodiments, the method involves measuring the bioactivity of TGF-β1 and TGF-β2 in an undigested powdered sample of nutritional product or raw protein source. In this embodiment, the method of the invention may comprise reconstituting a sample of nutritional product or raw protein source to from about 200 to about 300 mg/mL in distilled water or phosphate buffered saline (PBS). In another embodiment, the method involves reconstituting a sample of nutritional product or raw protein source to about 250 mg/mL in distilled water or PBS. In an embodiment, the reconstitution may comprise adding 1 gram of sample to 4 mL of distilled water or PBS.

The sample may then be acidified to a pH of from about 1 to about 2. In an embodiment, the sample may be acidified to a pH of about 1.5. The acidification step may be accomplished using any acid known in the art. In a particular embodiment, the acid may be 6M HCl. The ratio of sample:acid may be about 2:0.06. Thus, in an example, 2 mL sample may be acidified with 0.06 mL acid. The sample may be incubated at room temperature for about 3 hours and then centrifuged at 13,000 rpm for about 5 minutes.

The clear supernatant layer may then be collected and neutralized. The neutralization step may be accomplished using any base known in the art. In a particular embodiment, the base may be 6M NaOH. The base may be added to bring the sample to a pH of from about 7 to about 8. In a particular embodiment, the pH of the sample may be about 7 to about 7.5. The ratio of sample:base may be about 2.6:0.05. Thus, in an example, 2.6 mL sample may be acidified with 0.05 mL acid. The overall ratio of sample:acid:base may be 1:0.03:0.02 or 1.05.

As an alternative to acid activation, the reconstituted sample may be filtered. Thus, in an embodiment, after reconstitution, the sample may be incubated for about 1.5 hours at room temperature. The sample may then be centrifuged for about 5 minutes at about 13,000 rpm. In an embodiment, the sample may be centrifuged in this manner twice. The supernatant of the sample may then be collected and filtered using a 0.8/0.2 μm filter.

According to the method of the invention, the sample may then be run in the HT-2 bioassay with a dilution of 1:5 for the first point on each graph and 2-fold serial dilutions for the next nine points thereafter on each graph.

In a different embodiment, the bioactivity of TGF-β1 and TGF-β2 may be measured in a sample of nutritional product or raw protein source by first, if the sample is powdered, reconstituting the samples to from about 140 mg/mL to about 150 mg/mL. In an embodiment, the sample may be reconstituted to about 142 mg/mL. This reconstitution may comprise adding about 8.5 grams of the sample to about 2 fluid ounces of water. Alternatively, the reconstitution may comprise adding about 2.84 grams sample to about 20 mL water. If the sample is liquid, no reconstitution is necessary. In an embodiment, PPBS may replace water in the reconstitution.

In this embodiment, there is preferential fractionation of TGF-β in the soluble whey fraction (by about 10% to about 30%) of the reconstituted sample due to a lower reconstitution rate as demonstrated below in Table 1. As can be seen, the amount of whey-associated TGF-β2 is dependent on the reconstitution rate of the infant formula.

TABLE 1

| Sample | Weight | Casein fraction FD sample Weight | Whey fraction FD sample Weight | % Whey Fraction |
|---|---|---|---|---|
| Enf. Lip 250 mg/ml (1) | 5.0609 | 0.6044 | 2.7234 | 55 |
| Enf. Lip 250 mg/ml (2) | 5.0562 | 0.5369 | 2.8210 | |
| Enf. Lip 142 mg/ml (1) | 2.8463 | 0.1407 | 1.8545 | 64 |
| Enf. Lip 142 mg/ml (2) | 2.8408 | 0.1642 | 1.7570 | |

In this embodiment, the samples may then be centrifuged at 10,000 rpm for about 10 minutes. The pellet and top fat layer should be saved. Concentrated HCl may then be added to the supernatant to bring the pH to from about 2 to about 3. The sample may then be incubated for about 15 minutes at room temperature. The sample is again centrifuged at about 10,000 rpm for about 10 minutes. Again, the casein layer (pellet or top layer) should be saved along with the whey (supernatant) fraction. The supernatant layer may be neutralized with 50% NaOH to bring it to a pH of about 7 to about 7.5. The supernatant may then be centrifuged again at about 10,000 rpm for about 10 minutes. The pellets and supernatant fractions may then be freeze dried. The freeze-dried powder is reconstituted with water at a concentration of 500 mg/ml for use in the HT-2 cell bioassay.

In another embodiment, the method of the invention comprises measuring the bioactivity of TGF-β1 and TGF-β2 in a sample of undigested milk. In this example, the sample may be centrifuged three times at about 13,000 rpm for about 15 minutes. The sample may then be activated with 1N HCl (125 μL sample/25 μL 1N HCl) and incubated for about three hours at room temperature. The sample may then be neutralized with 1.N NaOH (125 μL sample/25 μL 1N NaOH). The sample may then be run in the HT-2 bioassay with 2-fold dilutions.

In an alternate embodiment, a sample of undigested milk may be prepared for the HT-2 bioassay by first activating it with 1N HCl (125 μL sample/25 μL 1N HCl) and incubating it at room temperature for about three hours. The sample may then be centrifuged at about 13,000 rpm for about 5 minutes. The supernatant may be collected and centrifuged at about 13,000 rpm for about 5 minutes. The sample may then be neutralized with 1N NaOH (125 μL sample/25 μL 1N NaOH). The sample may then be run in the HT-2 bioassay with 2-fold dilutions.

In another embodiment of the invention, the method may comprise measuring the bioactivity of TGF-β1 and TGF-β2 in a digested sample of nutritional product, raw protein source, or milk. In such an embodiment, the sample, if frozen, may be thawed at room temperature. The pH of the sample may be determined and then adjusted to a pH of from about 6.7 to about 6.8. The sample may then be centrifuged at 13,000 rpm for about 5 minutes. In an embodiment, the sample may be centrifuged twice in this manner. The supernatant layer may then be collected and run in the HT-2 bioassay with 2-fold dilutions.

In running the HT-2 bioassay, the protocol is as follows. The HT-2 cells should be in the log phase of growth. The standards and samples may then be diluted to working concentration with an assay media. Approximately 50 μL of assay media may be added to each well of a 96 well plate. Standards and samples may then added to each plate. To the first well, 25 μL may be added and 2-fold serially diluted from there. The last well may serve as a blank and may be filled with dilution media only. The samples may be run in duplicate.

In the next step, assay media may be added to each well in an amount of approximately 25 μL/well. HT-2 cells may then be harvested and washed with RPMI 3 times. The cells may then be resuspended at $4 \times 10^5$ cells/mL in the assay media. Approximately 25 μL of cells may be added to control wells (no IL-4 wells). IL-4 may then be added to the remaining cell suspension at about 30 ng/mL prior to adding 25 μL cells to the remaining wells.

The cells may then be incubated for about 48 hours at about 37° C. with 5% $CO_2$ in a humidified chamber. During the final 4-6 hours of incubation, approximately 10 μL of 0.1 mg/mL Resazurin may be added to each well. Following incubation, the fluorescence intensity may be measured with excitation wavelength at 560 nm and emission wavelength at 590 nm.

The equivalency of TGF-β bioactivity may be calculated using the plot of rhTGF-β bioactivity. In an example, the equivalency of TGF-β bioactivity is calculated for a sample having a TGF-β2 activity of 7175.3 pg/mL and $ED_{50}$ of 0.118 ng/mL of rhTGF-β2 on a generated plot shown in FIG. 1. A vertical line (1) may be drawn upward starting from the $ED_{50}$ of rhTGF-β2 (0.118 ng/mL in this example). A horizontal line (2) may be drawn starting from the intersection of the rhTGF-β2 line with the vertical line. A vertical line (3) may then be drawn where the horizontal line (2) intersects with the line of the sample. The dilution factor is determined based upon the intersection of the vertical line (3) with the x-axis. As shown in FIG. 1, the dilution factor in this case is 0.0048. Using this dilution factor and the $ED_{50}$ of 0.118 ng/mL, the equivalency of a sample can be calculated: (0.118/0.0048=24.583 ng/mL or 24583 pg/mL). To generate equivalency graphs, the calculated equivalency activity (pg/mL) can be plotted against the concentration of the sample (pg/mL) as measured by ELISA. Equivalency graphs and data are shown in FIG. 2A-D.

In a separate embodiment of the present invention, the bioactivity of TGF-β may be measured using a cellomics bioassay. TGF-β signals through cell surface receptors endowed with serine-/threonine kinase activity to intracellular signaling components known as Smads, which in turn modulate the activity of target genes in the nucleus. Smads can be subdivided into three types, receptor activated Smads (Smads 1, 2, 3, 5, 8), common or mediator Smads (Smad 4), and inhibitory Smads (Smads 6 and 7). Smad 2 and 3 are activated by TGF-β itself whereas Smad 1 and 5 are activated by other members of the transforming grown factor superfamily. Biological signal transduction is a complex process that involves activation and translocation of multiple signaling molecules. The majority of signaling events involve multiple interacting components and, in many instances, activation is coupled to movement of a target molecule from one location of a cell to another, transmitting a biological signal in the process.

The cellomics instrumentation used in the method of the invention may be any known in the art. In an embodiment, the instrumentation is Thermo Scientific Cellomics Molecular Translocation Bioapplication. Generally speaking, cellomics bioassays offer the ability to quantify intracellular movement of fluorescently labeled target molecules within single cells in a fully automated fashion. More specifically, cellomics offers a very powerful approach for analysis of transcription factor and kinase activation by monitoring movement between the cell cytoplasm and the nucleus.

The Smad redistribution assay discussed herein is designed for inhibitors of TGF-β1-induced Smad2 translocation by monitoring the translocation of a GFP-Smad2 fusion protein from the cytoplasm to the nucleus. TGF-β1 is used as a reference agonist, and compounds are assayed for their ability to inhibit TGF-β1-stimulated nuclear translocation of Smad2. The standard Smad cellomics study, however, is has not previously been adapted to measure the bioactivity of TGF-β in a sample of milk, nutritional product, or raw protein source. In this invention, the inventors have developed such a method.

In the first step of the method, powdered samples may be reconstituted with water or PBS at a concentration of 8.5 g/1 fl.oz or 0.284 g/mL. In another embodiment, the powdered samples may be reconstituted at a concentration of about 142 mg/mL. For liquids, such as milk, no reconstitution is necessary and the sample may be used as is. The working volume may be 1 ml.

The TGF-β may then be activated by addition of an acid, such as concentrated HCl, to reach a pH of from about 2 to about 3. For reconstituted powdered nutritional products, the amount of HCl may be from about 13 μL to about 16 μL. For milk, the amount of HCl may be from about 4 μL to about to 5 μL.

All samples may then be incubated for 15 minutes at room temperature. The samples may then be centrifuged at 10,000 rpm for about 10 min. The casein (pellet or top layer) and whey (supernatant) fractions may be saved.

The whey fraction/supernatant may then be neutralized with a base, such as 50% NaOH to reach a pH of about 7 to about 7.5. For nutritional products, the amount of NaOH may be from about 4 μL to about 8 μL. For milk, the amount of NaOH may be from about 1 μL to about 2 μL.

The samples may then be added to the cells as per the cellomics protocol for Smad2 bioassay for MDA-MB-468 cells. That protocol is described below. Cells are exposed to samples containing TGF-β for 90 minutes in the presence of 1% serum. After fixation, the cells are analyzed on the Cellomics ArrayScan VTI. The TGF-β response is calculated based on translocation of GFP-tagged Smad2 from the cytoplasm to the nucleus.

The following examples describe various embodiments of the present invention. Other embodiments within the scope of the claims herein will be apparent to one skilled in the art from consideration of the specification or practice of the invention as disclosed herein. It is intended that the specification, together with the examples, be considered to be exemplary only, with the scope and spirit of the invention being indicated by the claims which follow the examples. In the examples, all percentages are given on a weight basis unless otherwise indicated.

Example 1

This example illustrates the measurement of TGF-β bioactivity via a bioassay using HT-2 cells. A HT-2 subclone was obtained from the laboratory of Dr. P. Marrak (Kappler, J. W., et al., *J. Exp. Med.* 153:1198-214 (1981)). The subline had no detectable helper activity. The cells were in the log phase of growth.

Cell Growth and Preparation
Materials:
HT-2 Cells
Growth Medium
1. RPMI 1640
2. 10% FBS (JRH #: 12107-1000M)
3. 50 uM β-Mercaptoethanol
4. 2 mM L glutamine
5. 10 ng/mL rhIL-2
Cell Maintenance Protocol:
Cells were seeded at $2 \times 10^4$ cells/mL in Growth Medium. Cells were split every 2-3 days.
Sample Preparation A sample of human milk was obtained from a donor. The sample was activated by intermixing 125 μL of the sample with 25 μL 1N HCl. The sample was then incubated at room temperature for about three hours. The sample was then centrifuged at 13,000 rpm for 5 minutes. The supernatant was collected and centrifuged at about 13,000 rpm for about 5 minutes. The sample was then neutralized with 1.2N NaOH (125 μL sample/25 μL 1N NaOH).

HT-2 Bioassay
Materials:
HT-2 Cells
Assay Media
1. RPMI 1640
2. 10% FBS (JRH #: 12107-1000M)
3. 50 uM β-Mercaptoethanol
4. 2 mM L glutamine
rmIL-4
Dulbecco's PBS (Irvine #9240)
BSA (Sigma #A-7888)
Resazurin (R&D Catalog #AR002)
For Latent TGF-β activation: Glacial Acetic Acid (from Mallinckrodt Baker)
TGF-β Bioassay Protocol
1. The standards and samples were diluted to working concentration with the Assay Media:
   i. 50 μL Assay Media was added to each well of a 96 well plate.
   ii. The standards and samples were then added to the plate.
      1. 25 μL sample was added to the first well and was 3-fold serially diluted from there.
      2. The last well contained dilution media only (blank).
      3. The samples were run in duplicate.
   iii. 25 uL/well of Assay Media was added to all wells.
2. HT-2 cells were then harvested and washed with RPMI 3 times.
3. The cells were resuspended at $4 \times 10^5$ cells/mL in the Assay Media.
4. 25 μL of cells were added to control wells (no IL-4 wells). mIL-4 was added to the remaining cell suspension at 30 ng/mL prior to adding 25 μL cells to the remaining wells.
5. The plates were incubated for 48 hours at 37° C. with 5% $CO_2$ in a humidified chamber.
6. 10 μL of 0.1 mg/mL Resazurin was added to each well for the final 4-6 hours of incubation.
7. At the end of the incubation, the fluorescence intensity was measured with excitation wavelength at 560 nm and emission wavelength at 590 nm.

Figure 3:
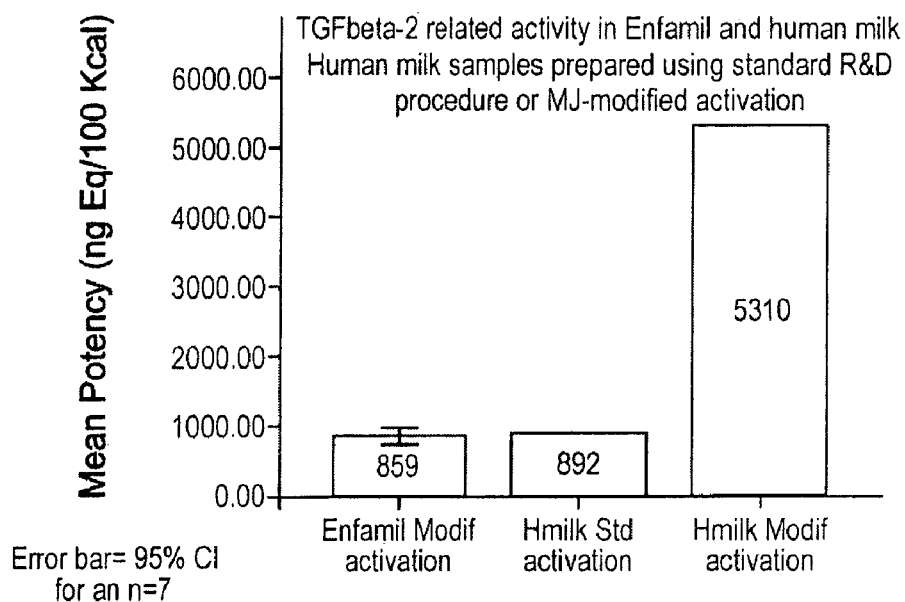
FIG. 3 shows TGF-β potency in Enfamil Lipil+ vs. human milk by activation method.

Simultaneously, samples of the same human milk were prepared and tested using standard HT-2 cell bioassay techniques. FIG. 3 illustrates the difference in bioactivity of human milk samples treated with the two different activation procedures. FIG. 3 illustrates that human milk samples prepared using the method of the present invention ("modified activation") had a bioactivity that was 5-fold higher than the human milk samples prepared according to the standard procedure ("standard activation"). Accordingly, it is evident that the method of the present invention provides a surprising and unexpected enhancement of TGF-β bioactivity.

Example 2

This example illustrates the cellomics method of measuring the bioactivity of TGF-β of the present invention.
The following samples were utilized in this example:
Infant Formula
i. 21 g of dry powder
ii. TGF-β2 concentration 0.05 ppm
Milk Protein Fraction Containing TGF-β2
i. 11.5 g of dry powder
ii. TGF-β2 concentration 0.9 ppm
Sample Preparation:

Samples were reconstituted at 0.142 g/ml with water. Samples were then centrifuged at 10,000 rpm for 10 min. The pellet and fat layer on top of solution was saved. TGF-β was activated by addition of concentrated HCl until pH was 2-3. Samples were then incubated for 15 minutes at room temperature. Following incubation, samples were centrifuged at 10,000 rpm for 10 minutes. The casein (pellet or top layer) and whey (supernatant) fractions were saved. The whey fraction/supernatant was neutralized with 50% NaOH until the pH was 7 to 7.5. The samples were then centrifuged at 10,000 rpm for 10 min.

Purified recombinant human TGF-β2 was purchased from Sigma (cat. no. T-2815), and dissolved and stored according to the manufacturer's instructions.

All compounds were profiled in 9-point half log concentration responses starting from 0.071 g/ml (final assay concentration) for the samples, and starting from 10 ng/ml (final assay concentration) for recombinant human TGF-β2. Compound activity was calculated relative to the negative and positive controls on the same plate.

TABLE 1

Plate map

| | 1 | 2 | 3 | 4 | 5 | 6 | 7 | 8 | 9 | 10 | 11 | 12 |
|---|---|---|---|---|---|---|---|---|---|---|---|---|
| A | So | - | Sample | Sample | Sample | Sample | Sample | Sample | Sample | Sample | Sample | Smax |
| B | So | - | Sample | Sample | Sample | Sample | Sample | Sample | Sample | Sample | Sample | Smax |
| C | So | - | Sample | Sample | Sample | Sample | Sample | Sample | Sample | Sample | Sample | Smax |
| D | So | - | Sample | Sample | Sample | Sample | Sample | Sample | Sample | Sample | Sample | Smax |
| E | Smax | - | Sample | Sample | Sample | Sample | Sample | Sample | Sample | Sample | Sample | So |
| F | Smax | - | Sample | Sample | Sample | Sample | Sample | Sample | Sample | Sample | Sample | So |
| G | Smax | - | Sample | Sample | Sample | Sample | Sample | Sample | Sample | Sample | Sample | So |
| H | Smax | - | Sample | Sample | Sample | Sample | Sample | Sample | Sample | Sample | Sample | So |

Layout of concentration-response plates in half log dilutions. One compound plate was used for each individual cell plate. So: negative control. Smax: positive control.

TABLE 2

| Assay | Negative control | Positive control |
|---|---|---|
| Smad2 | No addition | 10 ng/ml TGF-$\beta$2 |
| Smad3 | No addition | 10 ng/ml TGF-$\beta$2 |
| Smad4 | No addition | 10 ng/ml TGF-$\beta$2 |

Image analysis was performed using the Cellomics ArrayScan® V$^{TT}$ HCS Reader. Triplicate determinations were done at each concentration for generation of concentration response curves.

Average Z' factor of the assay plates was 0.78.

The infant formula was not fluorescent in the tested concentration range (tested by performing the assay in MDA-MB-468 cells that do not express GFP). Furthermore, there was no evident toxicity (samples did not cause any cell rounding or detachment).

TABLE 3

| | Smad2 assay | |
|---|---|---|
| Sample | EC$_{50}$ (g/ml) | Max activity (%) |
| TGF-$\beta$2 | 3.8E-11 | 99 |
| Infant formula, acid-activated | 4.4E-04 | 44 |
| Milk protein fraction, acid-activated | 5.3E-05 | 78 |

Figure 4A:
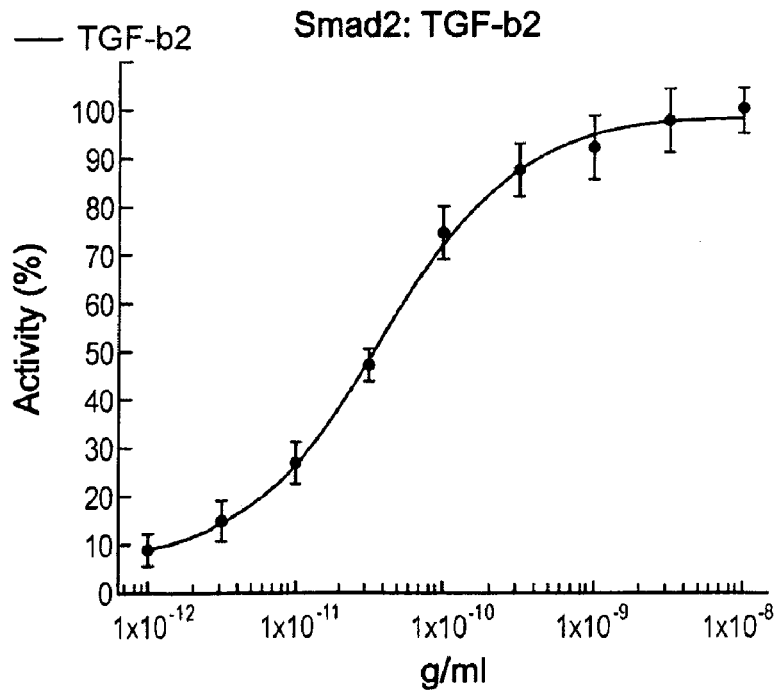
FIGS. 4A-C illustrate the results of the cellomics study.
Figure 4B:
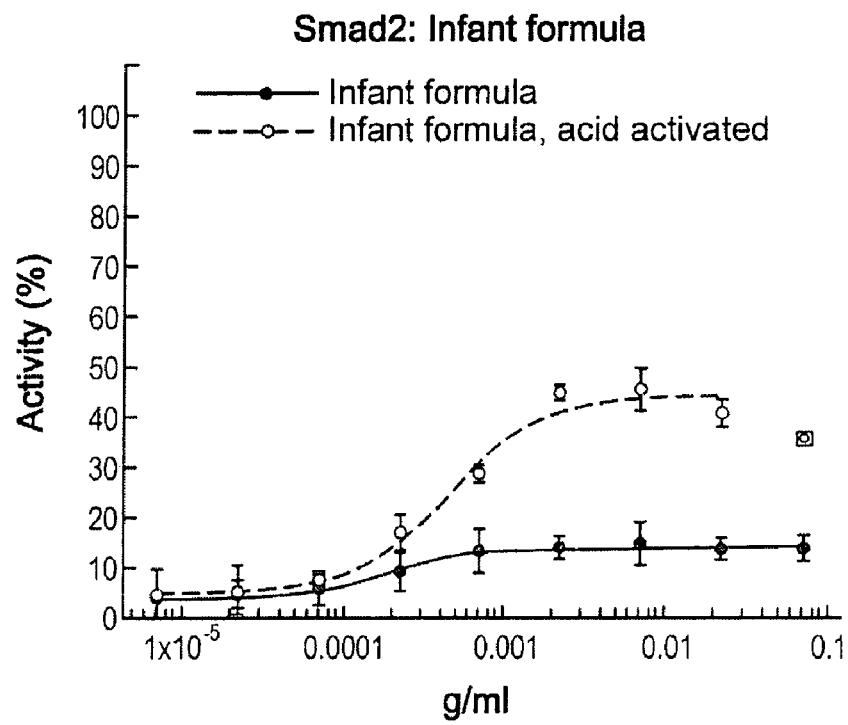
Figure 4C:
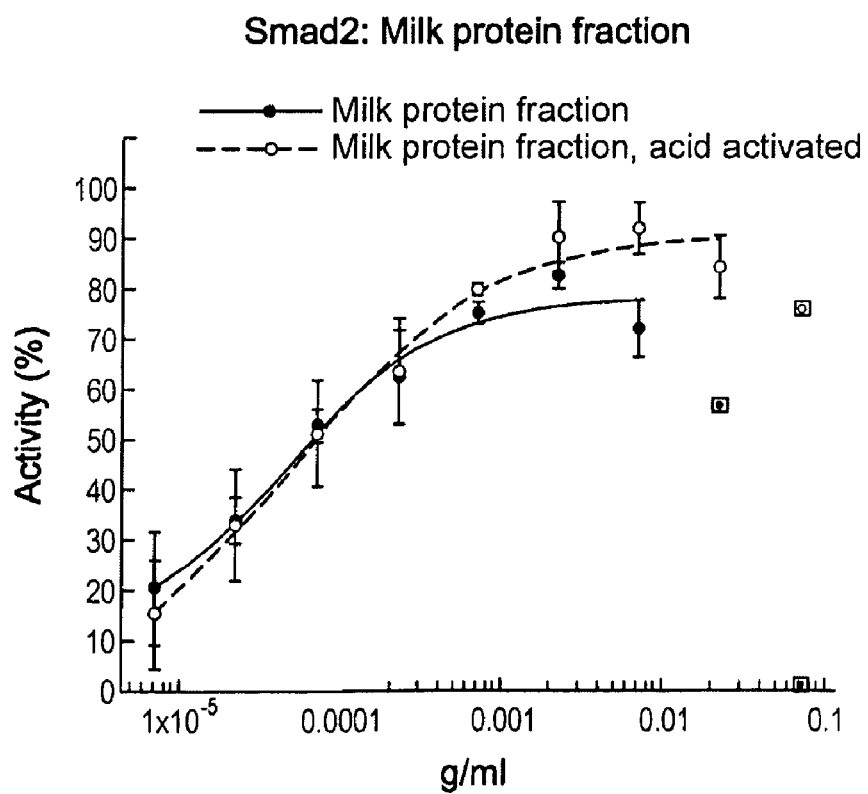

FIGS. 4A-C illustrates the results of the cellomics study.

An estimate of the TGF-$\beta$ concentration in the samples can be obtained by dividing the EC50 of the sample by the EC50 of purified recombinant human TGF-$\beta$2 (see Table 4).

TABLE 4

| | Mead Johnson | Smad2 assay | |
|---|---|---|---|
| Sample | ppm TGF$\beta$ (reported) | EC$_{50}$ (g/ml) | ppm TGF$\beta$ (calculated) |
| TGF-$\beta$2 | | 3.8E-11 | |
| Infant formula | 0.05 | 4.4E-04 | 0.09 |
| Milk protein fraction | 0.9 | 5.3E-05 | 0.7 |

All references cited in this specification, including without limitation, all papers, publications, patents, patent applications, presentations, texts, reports, manuscripts, brochures, books, internet postings, journal articles, periodicals, and the like, are hereby incorporated by reference into this specification in their entireties. The discussion of the references herein is intended merely to summarize the assertions made by their authors and no admission is made that any reference constitutes prior art. Applicants reserve the right to challenge the accuracy and pertinence of the cited references.

Although preferred embodiments of the invention have been described using specific terms, devices, and methods, such description is for illustrative purposes only. The words used are words of description rather than of limitation. It is to be understood that changes and variations may be made by those of ordinary skill in the art without departing from the spirit or the scope of the present invention, which is set forth in the following claims. In addition, it should be understood that aspects of the various embodiments may be interchanged both in whole or in part. For example, while methods for the production of a commercially sterile liquid nutritional supplement made according to those methods have been exemplified, other uses are contemplated. Therefore, the spirit and scope of the appended claims should not be limited to the description of the preferred versions contained therein.

What is claimed is:

1. A method for preparing a sample of powdered nutritional composition or powdered raw protein source for a HT-2 cell bioassay measuring TGF-$\beta$ activity, the method comprising:
    a. reconstituting the sample to a concentration of about 140 mg/mL to about 150 mg/mL;
    b. centrifuging the reconstituted sample to separate it into a supernatant layer and a pellet and retaining the supernatant layer;
    c. acidifying the supernatant layer to a pH of about 2 to about 3;
    d. incubating the supernatant layer for about 15 minutes at room temperature;
    e. centrifuging the supernatant layer to separate it into a second supernatant layer and a second pellet and retaining the second supernatant layer;
    f. neutralizing the second supernatant layer from step (e) to a pH of about 7 to about 7.5;
    g. centrifuging the second supernatant layer from step (f) to separate it into a third supernatant layer and a third pellet and retaining the third supernatant layer; and
    h. contacting the third supernatant layer with HT-2 cells.

2. The method of claim 1 wherein the concentration of the reconstituted sample is about 142 mg/mL.

3. The method of claim 1 wherein the nutritional composition is selected from the group consisting of a nutritional supplement, children's nutritional product, infant formula, and human milk fortifier.

4. The method of claim 1 wherein the raw protein source is selected from the group consisting of whey protein concentrate, non-fat dry milk, and casein protein.

5. The method of claim 1 wherein the reconstitution step comprises adding about 8.5 g of the sample to about 2 fl. oz. of water or phosphate buffered saline.

6. The method of claim 1 wherein the reconstitution step comprises adding about 2.84 g of the sample to about 20 mL of water or phosphate buffered saline.

7. The method of claim 1 wherein the acidification step comprises the addition of concentrated HCl.

8. The method of claim 1 wherein the neutralization step comprises the addition of 50% NaOH.

* * * * *